(12) United States Patent
Sawaki et al.

(10) Patent No.: US 7,700,123 B2
(45) Date of Patent: Apr. 20, 2010

(54) COSMETICS

(75) Inventors: Shigeru Sawaki, Osaka (JP); Shigetoyo Sawaki, Osaka (JP); Kiyoji Matsukawa, Osaka (JP); Yutaka Osawa, Osaka (JP); Ayako Hirota, Osaka (JP); Takako Ogura, Osaka (JP)

(73) Assignee: Technoble Co., Ltd., Osaka-Shi (JP)

( * ) Notice: Subject to any disclaimer, the term of this patent is extended or adjusted under 35 U.S.C. 154(b) by 623 days.

(21) Appl. No.: 10/466,322

(22) PCT Filed: Aug. 2, 2001

(86) PCT No.: PCT/JP01/06651

§ 371 (c)(1),
(2), (4) Date: Jul. 29, 2003

(87) PCT Pub. No.: WO02/060395

PCT Pub. Date: Aug. 8, 2002

(65) Prior Publication Data

US 2004/0052759 A1 Mar. 18, 2004

(30) Foreign Application Priority Data

Jan. 31, 2001 (JP) ............... 2001-024766
Feb. 27, 2001 (JP) ............... 2001-052438
Mar. 22, 2001 (JP) ............... 2001-082855
May 18, 2001 (JP) ............... 2001-150174

(51) Int. Cl.
*A61A 8/02* (2006.01)
*A01N 65/00* (2006.01)

(52) U.S. Cl. .................... 424/401; 424/750
(58) Field of Classification Search .............. None
See application file for complete search history.

(56) References Cited

U.S. PATENT DOCUMENTS 5,118,503 A * 6/1992 Sawai et al. .............. 424/750
5,219,597 A * 6/1993 Mok et al. ................ 426/28
5,571,516 A * 11/1996 Tezuka et al. ............ 424/401
6,046,022 A * 4/2000 Zhang et al. .............. 435/41

FOREIGN PATENT DOCUMENTS

| EP | 0345710 | | | 12/1989 |
|---|---|---|---|---|
| JP | 43-11290 | | | 5/1968 |
| JP | 53020441 | A | * | 2/1978 |
| JP | 2-53705 | | | 2/1990 |
| JP | 403044317 | A | * | 2/1991 |
| JP | 06199679 | | | 7/1994 |
| JP | 06217719 | A | * | 8/1994 |
| JP | 7-187992 | | | 7/1995 |
| JP | 7-197087 | | | 8/1995 |
| JP | 7-252129 | | | 10/1995 |
| JP | 7-267847 | | | 10/1995 |
| JP | 07305098 | | | 11/1995 |
| JP | 8-119870 | | | 5/1996 |
| JP | 08119870 | A | * | 5/1996 |
| JP | 09-182569 | | | 7/1997 |
| JP | 2000169891 | | | 6/2000 |
| JP | 2001-212445 | | | 8/2001 |
| JP | 2001-271096 | | | 10/2001 |

OTHER PUBLICATIONS

A Japanese Patent Office Communication for corresponding patent application No. 2001-150174 dated Dec. 6, 2004.

* cited by examiner

*Primary Examiner*—Sreeni Padmanabhan
*Assistant Examiner*—Layla Soroush
(74) *Attorney, Agent, or Firm*—Kratz, Quintos & Hanson, LLP

(57) ABSTRACT

Cosmetics containing an active component comprising lactic acid bacteria fermented rice obtained by fermenting rice with lactic acid bacteria; a skin brightening and caring agent comprising lactic acid bacteria fermented rice obtained by fermenting rice with lactic acid bacteria; and an emulsifier comprising as the main component lactic acid bacteria fermented rice obtained by fermenting rice with lactic acid bacteria substantially in the absence of sodium chloride. Thus, cosmetics can be obtained, which are excellent in emulsion stability and biological safety, have a good feeling when using and after using and further have a total beautifying effect of cosmetic treatment including an improving effect on hair texture, and brightening and caring effects on the skin.

12 Claims, 2 Drawing Sheets

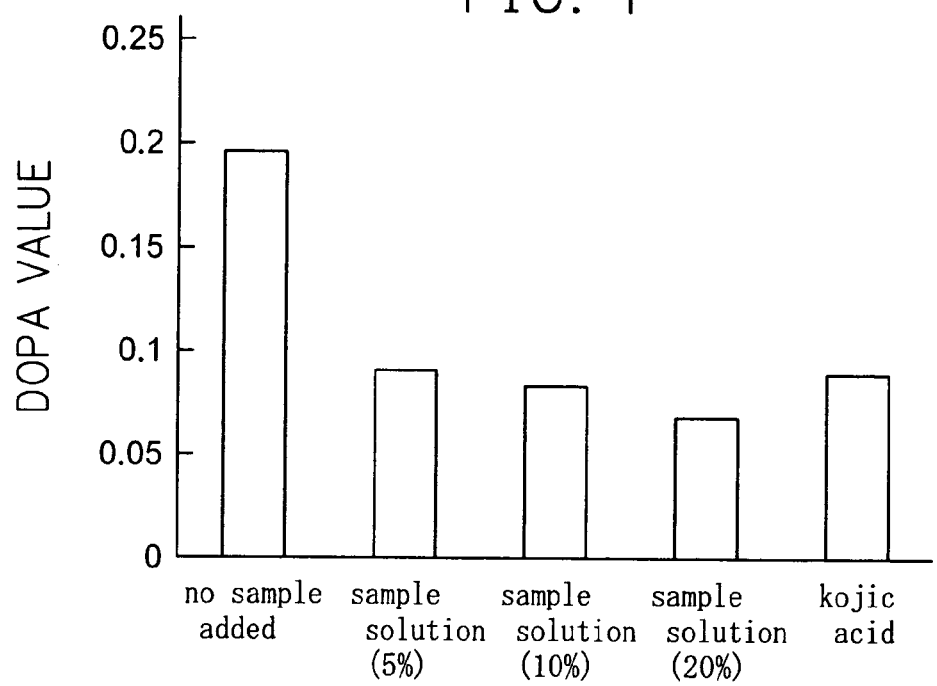
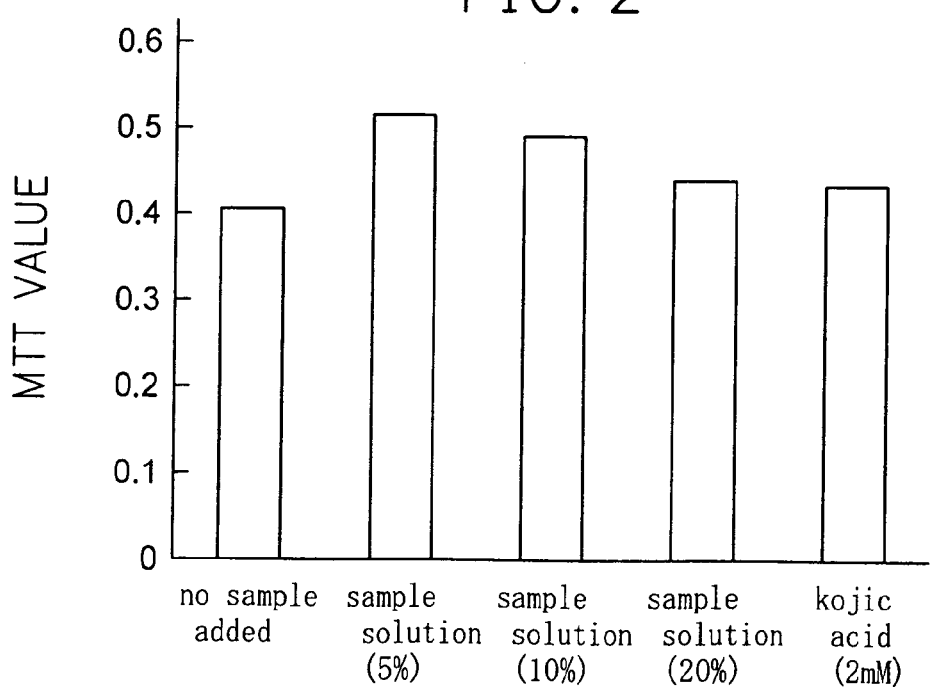

COSMETICS

CROSS-REFERENCE TO RELATED APPLICATION

This application is a national stage application under §371 of International application PCT/JP01/06651, filed on Aug. 2, 2001, which is hereby incorporated by reference.

TECHNICAL FIELD

The present invention relates to cosmetics containing processed rice. In particular, the present invention relates to cosmetics containing processed rice which is useful as a cosmetic base material such as an emulsifier and a stabilizer for emulsion, which exhibit excellent beautifying effects of cosmetic treatment including brightening and caring effects on the skin and improving effect on hair texture, and which is excellent in biological safety.

BACKGROUND ART

Conventionally, non-ionic surfactants such as polyoxyethylene alkyl ether and sorbitan fatty acid partial ester have been mainly used for emulsification in the field of cosmetics.

Since such surfactants inevitably raise irritation to the skin in greater and lesser degrees, attempts were made to evade such irritation by decreasing the amount of surfactants as much as possible or carrying out the emulsification without any surfactant depending on the situation. However, such attempts are not necessarily satisfied because there is a tendency to cause problems in the uniformity and stability of emulsion.

On the other hand, it has been proposed to prepare an emulsion which is highly safe to the skin by using, as an emulsifier, components come from a natural substance such as saponin, lecithin and enzyme-hydrolyzed stevioside, and a part of such proposals has been in practical use. However, the use of such components hardly adequate from viewpoints of emulsion stability, feeling when applied to the skin and easiness of manufacturing. Therefore, it is desired to develop a new emulsifier come from a natural substance which solves such disadvantages.

The above-mentioned biological safety is commonly required not only for emulsifier but also for all of other cosmetic components. If active components including a brightening component and a component for preventing skin aging could be found, which has both effectiveness and safety, it could be said that the active components have remarkably excellent utility.

As the result of diligent studies relating components to be used for cosmetics, especially emulsifier, in order to provide an agent having a high safety come from a natural substance, the inventors have found that the fermented rice is useful as a base material such as emulsifier and emulsion stabilizer, because fermented rice obtained by fermenting rice with lactic acid bacteria has good emulsifying effect, good emulsion-stabilizing effect and colloid stabilizing effect, and the fermented rice is highly safe to human body due to its less toxicity and less irritant to the skin owing to its rice origin, and the present invention has been accomplished. The inventors unexpectedly have found that the fermented rice is also useful as an agent for exhibiting beautifying effect of cosmetic treatment due to its excellent brightening and caring effects on the skin, and improving the hair texture.

DISCLOSURE OF INVENTION

The present invention relates to cosmetics containing an active component comprising lactic acid bacteria fermented rice obtained by fermenting rice with lactic acid bacteria.

The present invention also relates to a skin brightening and caring agent comprising lactic acid bacteria fermented rice obtained by fermenting rice with lactic acid bacteria.

Further, the present invention relates to an emulsifier comprising, as a main component, lactic acid bacteria fermented rice obtained by fermenting rice with lactic acid bacteria substantially in the absence of sodium chloride.

In this connection, the cosmetics of the present invention include quasi-drugs as well as what is called cosmetics.

BRIEF EXPLANATION OF DRAWINGS

FIG. 1 is a graph showing the Dopa value of each sample in Experimental Example 4.

FIG. 2 is a graph showing the MTT value of each sample in Experimental Example 4.

BEST MODE FOR CARRING OUT THE INVENTION

Figure 3:
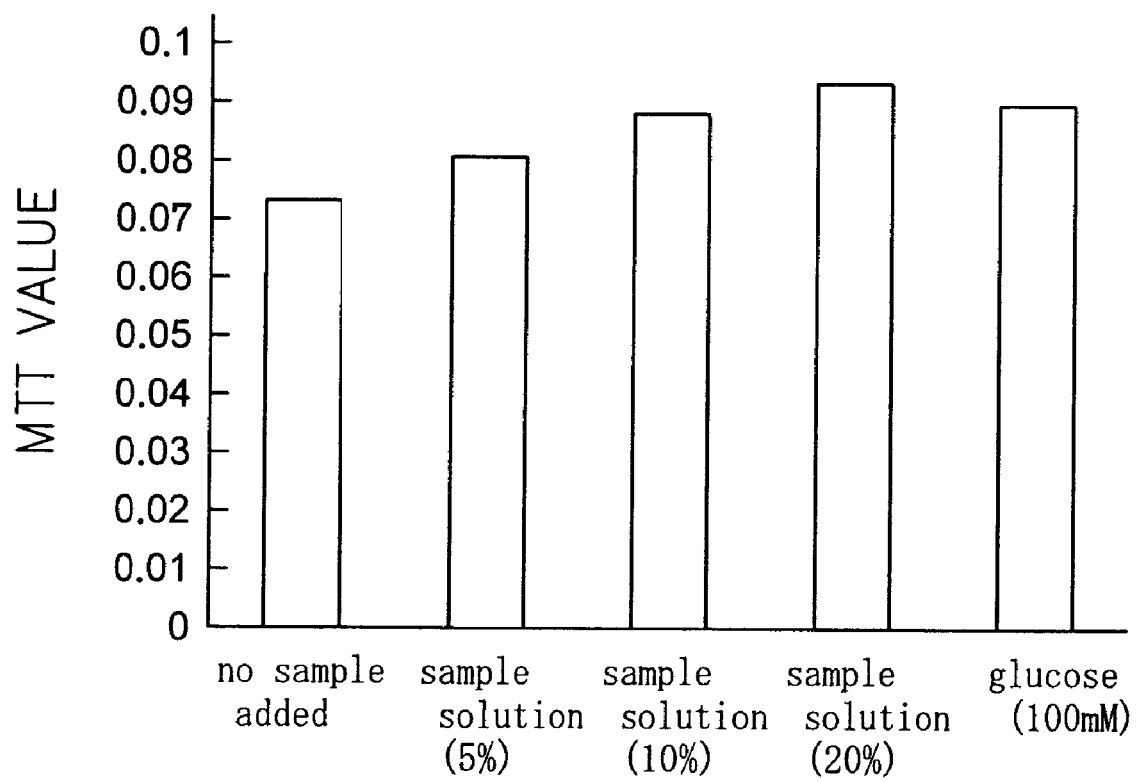
FIG. 3 is a graph showing the MTT value of each sample in Experimental Example 6.

The rice to be used for preparing lactic acid bacteria fermented rice being an active component of the present invention is not particularly limited, but includes unpolished rice, polished rice, processed rice. Polished rice and processed rice are generally used.

As type of the rice, non-glutinous rice and glutinous rice can be used. The processed rice includes low-allergen rice, low-protein rice (for example, low gluterin contained rice), enriched rice (for example, γ-aminobutyric acid-enriched rice) and the like. According to the purpose of use of the fermented rice and the subject to be applied, any rice can be selected and used.

Lactic acid bacteria to be used for fermentation of such raw rice include, for example, *Lactobacillus plantarum, Lactobacillus brevis, Lactobacillus casei, Lactobacillus cellobiosus, Lactobacillus vaccinostercus, Streptococcus faecalis, Bacillus coagulans* and the like. From the viewpoint of emulsifying ability of the lactic acid bacteria fermented rice, *Lactobacillus plantarum* is preferably used.

The fermentation of rice with such lactic acid bacteria can be carried out, for example, by the method mentioned hereinafter.

Firstly, miscellaneous bacteria which are an obstacle to fermentation with lactic acid bacteria are removed by appropriate means including rice-washing. The resulting rice is immerged into purified water in an amount of 1 to 5 times, and 1 to 4% by weight of saccharide and $10^7$ to $10^8$ cells/ml of lactic acid bacteria are added thereto. The resultant is subject to fermentation under anaerobic condition, around the optimum fermentation temperature of lactic acid bacteria for 1 to 7 days.

As the saccharide, glucose, fructose, galactose, sucrose and the like are used, especially fructose is used most preferably.

The solution containing the lactic acid bacteria fermented rice obtained in the above-mentioned fermentation step is directly subject to grind down process, and if necessary, the mixture is condensed. The resulting mixture or the condensed mixture can be added as an active component such as an emulsifier, an emulsifying auxiliary agent and a skin brightening and caring agent to cosmetics, or can be used as a main component of a skin brightening and caring agent or an emulsifier. In general, the lactic acid bacteria fermented rice is collected from the fermentation solution, washed with water, and grounded by using an appropriate means such as jet mill machine after adjustment of water content or without such adjustment, and if necessary, subjected to drying treatment. The resultant is added as an active component including an emulsifier, an emulsifying auxiliary agent and a skin brightening and caring agent to cosmetics, or used as a main component of a skin brightening and caring agent or an emulsifier.

In case where the fermentation step is carried out in the presence of an inorganic salt such as sodium chloride, the emulsifying ability of the resulting lactic acid bacteria fermented rice tends to decrease. Therefore, when the active component comprising the lactic acid bacteria fermented rice is an emulsifier or the lactic acid bacteria fermented rice is a main component of an emulsifier, it is preferred to use the lactic acid bacteria fermented rice obtained by fermenting rice with lactic acid bacteria substantially in the absence of the inorganic salt such as sodium chloride. However, even though the fermentation is carried out in the presence of the inorganic salt such as sodium chloride, the functions of the lactic acid bacteria fermented rice other than emulsifying ability, such as brightening and caring effects on the skin, and effect of improving the hair texture do not remarkably decrease. Therefore, when the lactic acid bacteria fermented rice is prepared in order to be added to cosmetics for the purpose of utilizing such functions or in order to be used as a skin brightening and caring agent, an inorganic salt such as sodium chloride may present in fermentation solution. Further, when the active component comprising the fermented rice is an emulsifying auxiliary agent, the lactic acid bacteria fermented rice obtained by fermenting rice with lactic acid bacteria in the presence of an inorganic salt such as sodium chloride can be used.

Although the emulsifying ability of the fermented rice obtained by fermenting rice with lactic acid bacteria in the presence of sodium chloride tend to decrease, the fermented rice exhibits good viscosity-increasing and stabilizing effects in the emulsification system or dispersion system, and therefore, it can be used for such purpose.

As shown in Experimental Examples 1 to 3 mentioned hereinafter, thus obtained lactic acid bacteria fermented rice has excellent emulsifying effect and emulsion-stabilizing effect, and provides an emulsified product having good emulsion stability, and is excellent in biological safety because of its low toxicity and low irritability. Therefore, the fermented rice is useful as an emulsifying agent or an emulsion-stabilizing agent for cosmetics. In addition, the fermented rice produces a potent inhibitory action on intracellular tyrosinase activity (Experimental Example 4), an inhibitory action on the skin pigmentary deposit based on the above action (Experimental Example 5), and an activating action on fibroblast (Experimental Example 6). Therefore, the fermented rice is useful as a novel skin brightening agent for preventing or improving pigmentary deposit such as blotches and freckles, or a skin-caring agent for preventing skin aging and improving rough dry skin.

Additionally, the lactic acid bacteria fermented rice to be used in the present invention has high water and moisture holding capacity and foam-stabilizing activity, and protection and adhesion effect on hair and skin. When the fermented rice is added to cleansing cosmetics such as shampoo and rinse, an excellent product can be obtained based on such properties, which gives creamy foam and excellent feeling when used, and prevents split hair and cracked hair by protecting and improving hair, and gives suitable wet feeling and gloss of hair to hair after use.

Based on the properties of the lactic acid bacteria fermented rice, such as high water and moisture holding capacity and adhesion effect on hair and skin, the cosmetics produced by adding the fermented rice have a good feeling when used (for example, expansion and smoothness on applying) and a good feeling after used (for example, wet feeling), and such characteristics are not observed in case of conventional base materials.

When the lactic acid bacteria fermented rice is added as an emulsifier to cosmetics, the fermented rice itself exhibits enough emulsifying ability and the resulting emulsified product shows an emulsion-stability enough that it can be practically used. When used together with a thickener, the fermented rice can further enhance the stability of the emulsified product.

Any thickener which was conventionally used for cosmetics can be used as the thickener in the present invention. Concrete examples of such thickener include, for instance, components derived from brown algae, green algae or red algae such as alginic acid, agar-agar, carrageenan and fucoidan; polysaccharides such as pectin and locust bean gum; gums such as xanthan gum, tragacanth gum and cyamoposis gum; cellulose derivatives such as carboxymethyl cellulose and hydroxyethyl cellulose; synthetic polymers such as polyvinyl alcohol, polyvinyl pyrrolidone, carboxyvinyl polymer, and acrylic acid methacrylic acid copolymer; hyaluronic acid and its derivatives, and polyglutamic acid and its derivatives.

Among them, in view point of emulsion-stability and safety which are the features of the lactic acid bacteria fermented rice, it is particularly preferred to use hyaluronic acid or its derivative, polyglutamic acid or its derivative, xanthan gum, or tragacanth gum. Components derived from brown algae, green algae or red algae such as alginic acid, agar-agar, carrageenan and fucoidan can also be preferably used.

When a thickener is used together with the lactic acid bacteria fermented rice, the amount of the thickener depends on the variety thereof. In general, the amount of the thickener (as the solid) is 1 to 100 weight parts, preferably 5 to 50 weight parts, per 100 weight parts of the fermented rice (as the solid). Taking into consideration the use and required property of the emulsified product, the optimum amount of the thickener can be selected from the above mentioned range.

In using a thickener together with the lactic acid bacteria fermented rice, the thickener may be used by premixing it with the fermented rice at a given ratio. Further, when cosmetics are emulsified by using the lactic acid bacteria fermented rice, the thickener may be added to an emulsification system before or after adding the fermented rice, or at the same time adding of the fermented rice. The thickener may be added after emulsifying.

The cosmetics of the present invention to which the lactic acid bacteria fermented rice is added include, for example, foundation cosmetics such as milky lotion, cream, lotion, essence and pack; make-up cosmetics such as lipstick, foundation, liquid foundation and makeup-pressed powder; cleansing cosmetics such as facial wash, shampoo and rinse; hair cosmetics such as hair treatment, hair conditioner, hair cream, hair dye and hair dressing; oral cosmetics such as tooth paste and mouth wash; bath agents, and quasi-drugs of various kinds of formulation, of course, but is not limited thereto.

In the cosmetics of the present invention, an amount of the lactic acid bacteria fermented rice to be added depends on the purpose of addition of the fermented rice, a kind of cosmetics and the like. For example, when the lactic acid bacteria fermented rice is used as the emulsifier, the amount of the fermented rice is generally 0.5 to 20% by weight (as solid portion of the fermented rice, as the same hereinafter), preferably 2 to 10% by weight to foundation cosmetics, make-up cosmetics, hair cosmetics and quasi-drugs; generally 1 to 30% by weight, preferably 5 to 20% by weight to the cleansing cosmetics; generally 0.5 to 20% by weight, preferably 2 to 10% by weight to oral cosmetics. In this case, when a thickener is used together, the amount of the lactic acid bacteria fermented rice can be reduced to 40 to 80% of the amount in the use of the fermented rice alone.

When the fermented rice is used as an emulsion-stabilizing agent, the amount of the fermented rice is generally 0.1 to 20% by weight, preferably 0.5 to 10% by weight to foundation cosmetics, make-up cosmetics, hair cosmetics, oral cosmetics and quasi-drugs; generally 1 to 30% by weight, preferably 5 to 20% by weight to cleansing cosmetics.

On the other hand, when the lactic acid bacteria fermented rice is used as a skin brightening and caring agent, the amount of the fermented rice is generally 0.1 to 10% by weight, preferably 0.5 to 5% by weight to foundation cosmetics, make-up cosmetics and quasi-drugs; generally 1 to 30% by weight, preferably 3 to 15% by weight to bath agents.

In case of preparing the cosmetics to which the lactic acid bacteria fermented rice of the present invention is added, as the components of the cosmetics, any component which is conventionally used for cosmetics, for example, oil components, surfactants, moisturizing agents, thickeners, a preventative and bactericidal agents, powder components, ultraviolet absorbents, antioxidants, pigments and physiologically active components can be used alone or in combination thereof.

Oil components include, for example, vegetable fats and oils such as olive oil, jojoba oil, caster oil, soybean oil, rice oil, rice germ oil, coconut oil, palm oil, cacao oil, meadowfoam oil, shea butter and tea tree oil; animal fats and oils such as mink oil and turtle oil; wax such as bee wax, carnauba wax, rice wax and lanolin; hydrocarbons such as liquid paraffin, waseline, paraffin wax and squalane; fatty acids such as myristic acid, palmitic acid, stearic acid, oleic acid and isostearic acid; higher alcohols such as lauryl alcohol, sethanol and stearyl alcohol; synthetic esters and synthetic triglycerides such as isopropyl myristate, isopropyl palmitate, butyl oleate, 2-ethylhexylgyceride, and a higher fatty acid octyl dodecyl ester (for example, octyl dodecyl stearate).

When the lactic acid bacteria fermented rice is added as an emulsifier, surfactant is not indispensable. In case of using the surfactant, it is preferred to use a small amount of a surfactant having good biological safety such as sucrose fatty acid esters, lecithin and enzyme-hydrolyzed stevioside. In case where the lactic acid bacteria fermented rice is added as an emulsion-stabilizing agent or a component for brightening and caring the skin, and emulsification is partially or wholly dependent on a conventional surfactant, useful surfactants include not only the above-mentioned surfactants such as sucrose fatty acid esters but also non-ionic surfactants such as polyoxyethylene alkyl ethers, polyoxyethylene fatty acid esters, polyoxyethylene sorbitan fatty acid esters, glycerin fatty acid esters, polyglycerin fatty acid esters, polyoxyethylene glycerin fatty acid esters, polyoxyethylene hydrogenated caster oil and polyoxyethylene sorbitol fatty acid esters; anionic surfactants such as fatty acid salts, alkyl sulfate, alkylbenzenesulfonate, polyoxyethylene alkyl ether sulfate, polyoxyethylene aliphatic amine sulfate, polyoxyethylene alkylphenyl ether sulfate, polyoxyethylene alkyl ether phosphate, α-sulfonated fatty acid alkyl ester salts, and polyoxyethylene alkylphenyl ether phosphate; cationic surfactants such as quaternary ammonium salts, primary, secondary or tertiary aliphatic amine salts, trialkyl benzyl ammonium salts, alkylpyridinium salts, 2-alkyl-1-alkyl-1-hydroxyethylimidazolinium salts, N,N-dialkylmorpholinium salts, and polyethylene polyamine fatty acid amide salts; amphoteric surfactants such as N,N-dimethyl-N-alkyl-N-carboxymethylammonio betaine, N,N,N-trialkyl-N-alkylene-ammoniocarboxy betaine and N-acylamidopropyl-N',N'-dimethyl-N'-β-hydroxypropylammoniosulfo betaine.

As the moisturizing agent there are included, for example, glycerin, propylene glycol, dipropylene glycol, 1,3-butylene glycol, polyethylene glycol, sorbitol, xylitol and sodium pyrrolidone-carbonate, and further sugars, hyaluronic acid and its derivatives, lactic acid, urea, various amino acids and derivatives thereof.

As the thickener, there are included the above-mentioned constituent from algae, polysaccharide, gum, cellulose derivatives, hyaluronic acid and derivatives thereof.

As the preservative and bactericidal agent, there are included, for example, urea; paraoxybenzoic acid esters such as methyl paraoxybenzoate, ethyl paraoxybenzoate, propyl paraoxybenzoate, butyl paraoxybenzoate; phenoxyethanol, dichlorophen, hexachlorophen, chlorohexidine hydrochloride, benzalkonium chloride, salicylic acid, ethanol, undecylenic acid, phenols and Germall (imidazolidinylurea).

The powder components include, for xample, sericite, titanium oxide, talc, kaolin, bentonite, zinc oxide, magnesium carbonate, magnesium oxide, zirconium oxide, barium sulfate, silicic acid anhydride, mica, nylon powder and silk powder.

The ultraviolet absorbents include, for example, ethyl paraaminobenzoate, ethyhexyl paradimethylaminobenzoate, amyl salicylate and its derivatives, 2-ethylhexyl paramethoxycinnamate, octyl cinnamate, oxybenzone, 2,4-dihydroxybenzophenone, 2-hydroxy-4-methoxybenzophenone-5-sulfonate, 4-tertiary butyl-4-methoxybenzoyl-methane, 2-(2-hydroxy-5-methylphenyl)benzotriazole, urocanic acid and ethyl urocanate.

The antioxidants include, for example, butyl hydroxyanisole, butyl hydroxytoluene, propyl gallate and vitamin E and its derivatives.

The physiologically active components includes, as a component for brightening and caring the skin, for example, kojic acid and its derivatives, ascorbic acid and its derivatives, arbutin and its derivatives, ellagic acid and its derivatives, resorcinol derivatives, mulberry bark extract, strawberry geranium extract, rice bran extract and 2,5-dihydroxybenzoic acid derivatives; as components for preventing skin aging and improving roughing skin (caring the skin), for example, collagen, nicotinic acid and its derivatives, vitamin E and its derivatives, α-hydroxylic acids, diisopropylamine dichloroacetate, γ-amino-β-hydroxybutylic acid and galenical extract such as gentian extract.

The above-mentioned kojic acid derivatives include, for example, kojic acid esters such as kojic acid monobutylate, kojic acid monocaprate, kojic acid monopalmitate and kojic acid dibutylate, and kojic acid ethers. The ascorbic acid derivatives include, for example, ascorbic acid ester salts such as L-ascorbic acid-2-phosphate sodium, L-ascorbic acid-2-phosphate magnesium, L-ascorbic acid-2-sulfate sodium and L-ascorbic acid-2-sulfate magnesium, and ascorbic acid sugar derivatives such as L-ascorbic acid-2-glycoside(2-O-α-D-glucopyranosyl-L-ascorbic acid) and L-ascorbic acid-5- glycoside(5-O-α-D-glucopyranosyl-L-ascorbic acid). The resorcinol derivatives include, for example, 4-n-butylresorcinol and 4-isoamylresorcinol. The 2,5-dihydroxybenzoic acid derivatives include, for example, 2,5-diacetoxybenzoic acid, 2-acetoxy-5-hydroxybenzoic acid and 2-hydroxy-5-propyonyloxybenzoic acid. The nicotinic acid derivatives include, for example, nicotinic acid amide and benzyl nicotinate. The vitamin E derivatives include, for example, vitamin E nicotinate and vitamin E linolenate. The α-hydroxylic acids include, for example, lactic acid, citric acid and α-hydroxyoctanoic acid.

The present invention is explained in detail by means of Preparation Examples, EXAMPLES (Prescription Examples) and Experimental Examples, but is not limited thereto. Hereinafter, "part(s)" and "%" mean "part(s) by weight" and "% by weight", respectively.

PREPARATION EXAMPLE 1

10 kg of polished rice was washed with water, put into a fermentation tank together with 40 kg of a solution prepared by dispersing 2% of fructose and *Lactobacillus plantarum* ($10^8$ cells/ml) in water, whereby fermentation was carried out at 37° C. for 3 days under nitrogen atmosphere. After the fermentation was completed, the fermented rice was collected by filtration, washed with water and then ground by a jet mill machine. The water content in the fermented rice was adjusted to at most 13% by using a fluidized bed dryer to give the lactic acid bacteria fermented rice powder.

PREPARATION EXAMPLE 2

Lactic acid bacteria fermented rice powder was obtained in the same manner as in Preparation Example 1 except that low-allergen rice (trade name: Fine rice) was used as rice instead of the polished rice.

PREPARATION EXAMPLE 3

Lactic acid bacteria fermented rice powder was obtained in the same manner as in Preparation Example 1 except that *L. casei* was used as lactic acid bacteria instead of *L. plantarum*.

PREPARATION EXAMPLE 4

Lactic acid bacteria fermented rice powder was obtained in the same manner as in Preparation Example 1 except that glucose was used as sugar instead of fructose.

PREPARATION EXAMPLE 5

10 kg of polished rice was washed with water, put into a fermentation tank together with 40 kg of a solution prepared by dispersing 2% of fructose and *Lactobacillus plantarum* ($10^8$ cells/ml) in water, whereby fermentation was carried out at 37° C. for 3 days under nitrogen atmosphere. After the fermentation was completed, the fermented rice was obtained by filtration and washed with water. 8 kg of the thus obtained fermented rice was re-dispersed in 30 kg of water, and then ground by a grind down machine to make it nearly uniform, whereby the lactic acid bacteria fermented rice dispersion was obtained.

PREPARATION EXAMPLE 6

2 kg of the lactic acid bacteria fermented rice obtained in Preparation Example 1 and 0.5 kg of hyaluronic acid were kneaded with 0.5 kg of 1,3-butyleneglycol, whereby white wet powder was obtained.

PREPARATION EXAMPLE 7

2 kg of the lactic acid bacteria fermented rice obtained in Preparation Example 1 and 0.5 kg of xanthan gum were kneaded with 0.5 kg of 1,3-butyleneglycol, whereby white wet powder was obtained.

PREPARATION EXAMPLE 8

2 kg of the lactic acid bacteria fermented rice obtained in Preparation Example 1 and 0.5 kg of xanthan gum were kneaded with 2.5 kg of 1,3-butyleneglycol, whereby white paste was obtained.

PREPARATION EXAMPLE 9

10 kg of polished rice was washed with water, put into a fermentation tank together with 40 kg of a solution prepared by dispersing 2.0% of fructose, 4.0% of sodium chloride and *Lactobacillus plantarum* ($10^8$ cells/ml) in water, whereby fermentation was carried out at 37° C. for 3 days under nitrogen atmosphere. After the fermentation was completed, the fermented rice was obtained by filtration, washed with water, and ground by a jet mill machine. The water content in the fermented rice was adjusted to at most 13% by using a fluidized bed dryer to give the lactic acid bacteria fermented rice powder containing sodium chloride.

EXAMPLE 1

| Cream | |
|---|---|
| | Part(s) |
| (Component A) | |
| Liquid paraffin | 5.0 |
| Olive oil | 4.0 |
| Paraffin | 5.0 |
| Cetanol | 2.0 |
| Butylparaben | 0.1 |
| (Component B) | |
| The lactic acid bacteria fermented rice powder obtained in Preparation Example 1 | 5.0 |
| 1,3-Butylene glycol | 10.0 |
| Methylparaben | 0.1 |
| Purified water | the volume to allow a total amount to be 100 parts |
| (Component C) | |
| Perfume | 0.3 |

After each of Component A and Component B was warmed to 80° C. or higher, the Component B was added to the Component A. The resultant was stirred and homogenized for 2 minutes with PHYSCOTRON (5000 rpm).

After the resulting homogenate was cooled to 50° C., Component C was added thereto. The resultant was mixed with stirring and then further cooled to 30° C. or lower to give a homogenous cream.

EXAMPLE 2

Milky lotion

|  | Part(s) |
|---|---|
| (Component A) | |
| Liquid paraffin | 5.0 |
| Olive oil | 4.0 |
| Squalane | 5.0 |
| Butylparaben | 0.1 |
| (Component B) | |
| The lactic acid bacteria fermented rice powder obtained in Preparation Example 1 | 5.0 |
| 1,3-Butylene glycol | 10.0 |
| Methylparaben | 0.1 |
| Purified water | the volume to allow a total amount to be 100 parts |
| (Component C) | |
| Perfume | 0.3 |

After each of Component A and Component B was warmed to 80° C. or higher, the Component B was added to the Component A. The resultant was stirred and homogenized for 2 minutes with PHYSTRON (5000 rpm).

After the resultant was cooled to 50° C., Component C was added thereto. The resultant was mixed with stirring and then further cooled to 30° C. or lower to give a homogenous milky lotion.

EXAMPLE 3

Face lotion

|  | Part(s) |
|---|---|
| (Component A) | |
| Olive oil | 1.0 |
| Butylparaben | 0.1 |
| (Component B) | |
| The lactic acid bacteria fermented rice powder obtained in Preparation Example 1 | 1.0 |
| Ethanol | 5.0 |
| Glycerin | 5.0 |
| 1,3-Butylene glycol | 5.0 |
| Methylparaben | 0.1 |
| Purified water | the volume to allow a total amount to be 100 parts |
| (Component C) | |
| Perfume | 0.3 |

After each of Component A and Component B was warmed to 80° C. or higher, the Component B was added to the Component A. The resultant was stirred and homogenized for 2 minutes with PHYSTRON (5000 rpm).

After the resultant was cooled to 50° C., Component C was added thereto. The resultant was mixed with stirring and then further cooled to 30° C. or lower to give a milk-white face lotion.

EXAMPLE 4

Essence

|  | Part(s) |
|---|---|
| (Component A) | |
| Olive oil | 1.0 |
| Butylparaben | 0.1 |
| (Component B) | |
| The lactic acid bacteria fermented rice powder obtained in Preparation Example 1 | 2.0 |
| Ethanol | 5.0 |
| Hyaluronic acid | 0.3 |
| 1,3-Butylene glycol | 5.0 |
| Methylparaben | 0.1 |
| Purified water | the volume to allow a total amount to be 100 parts |
| (Component C) | |
| Perfume | 0.3 |

After each of Component A and Component B was warmed to 80° C. or higher, the Component B was added to the Component A. The resultant was stirred and homogenized for 2 minutes with PHYSCOTRON (5000 rpm).

After the resultant was cooled to 50° C., Component C was added thereto. The resultant was mixed with stirring and then further cooled to 30° C. or lower to give a milk-white essence.

EXAMPLE 5

Milky Lotion

Homogeneous milky lotion was obtained in the same manner as in EXAMPLE 2 except that 5.0 parts of the lactic acid bacteria fermented rice powder obtained in Preparation Example 2 was used in Component B of EXAMPLE 2 instead of 5.0 parts of the lactic acid bacteria fermented rice powder obtained in Preparation Example 1.

EXAMPLE 6

Milky Lotion

Homogeneous milky lotion was obtained in the same manner as in EXAMPLE 2 except that 5.0 parts of the lactic acid bacteria fermented rice powder obtained in Preparation Example 3 was used in Component B of EXAMPLE 2 instead of 5.0 parts of the lactic acid bacteria fermented rice powder obtained in Preparation Example 1.

EXAMPLE 7

Milky Lotion

Homogeneous milky lotion was obtained in the same manner as in EXAMPLE 2 except that 5.0 parts of the lactic acid bacteria fermented rice powder obtained in Preparation Example 4 was used in Component B of EXAMPLE 2 instead of 5.0 parts of the lactic acid bacteria fermented rice powder obtained in Preparation Example 1.

EXAMPLE 8

Milky Lotion

Homogeneous milky lotion was obtained in the same manner as in EXAMPLE 2 except that 15.0 parts of the lactic acid bacteria fermented rice suspension obtained in Preparation Example 5 was used in Component B of EXAMPLE 2 instead of 5.0 parts of the lactic acid bacteria fermented rice powder obtained in Preparation Example 1.

EXAMPLE 9

Milky Lotion

Homogeneous milky lotion was obtained in the same manner as in EXAMPLE 2 except that 2.0 parts of the lactic acid bacteria fermented rice powder obtained in Preparation Example 1 and 0.5 part of xanthan gum was used in Component B of EXAMPLE 2 instead of 5 parts of the lactic acid bacteria fermented rice powder obtained in Preparation Example 1.

EXAMPLE 10

Milky Lotion

Homogeneous milky lotion was obtained in the same manner as in EXAMPLE 2 except that 2.5 parts of the paste obtained in Preparation Example 8 was used in Component B of EXAMPLE 2 instead of 5.0 parts of the lactic acid bacteria fermented rice powder obtained in Preparation Example 1.

EXAMPLE 11

| Hair treatment | Part(s) |
|---|---|
| (Component A) | |
| Stearyltrimethylammonium chloride | 5.0 |
| Glyceryl monostearate | 1.0 |
| Sethanol | 3.0 |
| Octyldodecanol | 2.0 |
| (Component B) | |
| The lactic acid bacteria fermented rice powder obtained in Preparation Example 1 | 5.0 |
| 1,3-Butylene glycol | 5.0 |
| Hydrolyzed collagen powder | 0.5 |
| Methylparaben | 0.1 |
| Purified water | the volume to allow a total amount to be 100 parts |
| (Component C) | |
| Perfume | 0.3 |

After each of Component A and Component B was warmed to 80° C. or higher, the Component B was added to the Component A. The resultant was stirred and homogenized for 2 minutes with PHYSCOTRON (5000 rpm).

After the resultant was cooled to 50° C., Component C was added thereto. The resultant was mixed with stirring and further cooled to 30° C. or lower.

EXAMPLE 12

| Hair cream | Part(s) |
|---|---|
| (Component A) | |
| Squalane | 15.0 |
| Vaseline | 15.0 |
| Bee wax | 2.0 |
| Methylparaben | q.s. |
| (Component B) | |
| Glycerine | 3.0 |
| 1,3-Butylene glycol | 3.0 |
| Xanthan gum | 0.1 |
| The lactic acid bacteria fermented rice powder obtained in Preparation Example 1 | 5.0 |
| Polyoxyethylene hydorogenated caster oil | 3.0 |
| Purified water | the volume to allow a total amount to be 100 parts |
| (Component C) | |
| Perfume | q.s. |

By warming to 80° C., Component A was melted and Component B was dissolved, and then both the Components were combined and homogenized for 2 minutes with PHYSCOTRON (5000 rpm). The resultant was cooled with stirring, and Component C was added thereto at 50° C. The resultant was further cooled to 30° C.

EXAMPLE 13

| Hair dyeing agent . Dye base | Part(s) |
|---|---|
| (Component A) | |
| Oxide dye | 3.5 |
| Oleic acid | 20.0 |
| Stearic acid diethanolamide | 3.0 |
| Polyoxyethylene (50) oleyl ether | 1.0 |
| (Component B) | |
| The lactic acid bacteria fermented rice powder obtained in Preparation Example 1 | 3.0 |
| 1,3-Butylene glycol | 10.0 |
| Isopropanol | 10.0 |
| An aqueous ammonia solution (28%) | 10.0 |
| Sodium sulfite | 0.5 |
| Purified water | the volume to allow a total amount to be 100 parts |

After each of Component A and Component B was warmed to 80° C. or higher, the Component B was added to the Component A. The resultant was stirred and homogenized for 2 minutes with PHYSCOTRON (5000 rpm).

The resultant was cooled to 30° C. or lower with stirring.

EXAMPLE 14

Liquid foundation

| | Part(s) |
|---|---|
| (Component A) | |
| Stearic acid | 2.5 |
| Sethanol | 0.5 |
| Glyceryl monostearate | 2.0 |
| Ranolin | 2.0 |
| Squalane | 3.0 |
| Isopropyl myristate | 8.0 |
| Propylparaben | 0.1 |
| (Component B) | |
| The lactic acid bacteria fermented rice powder obtained in Preparation Example 1 | 3.0 |
| Xanthan gum | 0.3 |
| 1,3-Butylene glycol | 5.0 |
| Triethanolamine | 1.0 |
| Methylparaben | 0.1 |
| Purified water | the volume to allow a total amount to be 100 parts |
| (Component C) | |
| Titanium oxide | 8.0 |
| Talc | 4.0 |
| Coloring pigment | q.s. |
| (Component D) | |
| Perfume | 0.3 |

Component C was mixed and pulverized with a grinder. Component B was mixed, and the pulverized Component C was added thereto. The resultant was homogeneously dispersed with a colloid mill. After each of Component A and the homogeneously dispersed Components B and C were warmed to 80° C., the Component A was added to Components B and C with stirring, and the resultant was homogenized for 2 minutes with PHYSCOTRON (5000 rpm). After the resultant was cooled to 50° C., Component D was added thereto. The resultant was mixed with stirring, and then further cooled to 30° C. or lower with stirring.

EXAMPLE 15

Cream foundation

| | Part(s) |
|---|---|
| (Component A) | |
| Stearic acid | 5.0 |
| Sethanol | 2.0 |
| Glyceryl monostearate | 3.0 |
| Liquid paraffin | 5.0 |
| Squalane | 3.0 |
| Isopropyl myristate | 8.0 |
| Propylparaben | 0.1 |
| (Component B) | |
| The lactic acid bacteria fermented rice powder obtained in Preparation Example 1 | 3.0 |
| Sorbitol | 3.0 |

-continued

Cream foundation

| | Part(s) |
|---|---|
| 1,3-Butylene glycol | 5.0 |
| Triethanolamine | 1.5 |
| Methylparaben | 0.1 |
| Purified water | the volume to allow a total amount to be 100 parts |
| (Component C) | |
| Titanium oxide | 8.0 |
| Talc | 2.0 |
| Kaolin | 5.0 |
| Bentonite | 1.0 |
| Coloring pigment | q.s. |
| (Component D) | |
| Perfume | 0.3 |

Component C was mixed and pulverized with a grinder. Component B was mixed, and the pulverized Component C was added thereto. The resultant was homogeneously dispersed with a colloid mill. After each of Component A and the homogeneously dispersed Components B and C was warmed to 80° C., the Component A was added to the Components B and C with stirring, and the resultant was homogenized for 2 minutes with PHYSCOTRON (5000 rpm). After the resultant was cooled to 50° C., Component D was added thereto. The resultant was mixed with stirring, and then further cooled to 30° C. or lower with stirring.

EXAMPLE 16

Cream rinse

| | Part(s) |
|---|---|
| (Component A) | |
| Polyoxyethylen (10) hydorogenated caster oil | 1.0 |
| Distearyldimethylammonium chloride | 1.5 |
| Stearyltrimethylammonium chloride | 2.0 |
| Glyceryl 2-ethylhexanate | 1.0 |
| Sethanol | 3.2 |
| Stearyl alcohol | 1.0 |
| Methylparaben | 0.1 |
| (Component B) | |
| The lactic acid bacteria fermented rice powder obtained in Preparation Example 1 | 15.0 |
| 1,3-Butylene glycol | 5.0 |
| Purified water | the volume to allow a total amount to be 100 parts |

By warming to 80° C., Component A was homogeneously melted and Component B was homogeneously dissolved, and then the Component B was added to the Component A. The resultant was cooled to room temperature with continuously stirring.

EXAMPLE 17

Cream shampoo

| | Part(s) |
|---|---|
| (Component A) | |
| N-Coconut oil fatty acid methyltaurine sodium salt | 10.0 |
| Sodium polyoxyethylene (3) alkyl ether sulfate | 20.0 |
| Lauryl dimethylaminoacetic acid betain | 10.0 |
| Coconut oil fatty acid diethanolamide | 4.0 |
| Methylparaben | 0.1 |
| (Component B) | |
| Citric acid | 0.1 |
| The lactic acid bacteria fermented rice powder obtained in Preparation Example 1 | 15.0 |
| 1,3-Butylene glycol | 2.0 |
| Purified water | the volume to allow a total amount to be 100 parts |

After each of Component A and Component B was homogeneously dissolved by warming it to 80° C., the Component B was added to the Component A, and the resultant was cooled to room temperature with continuously stirring.

EXAMPLE 18

Body shampoo

| | Part(s) |
|---|---|
| (Component A) | |
| N-Laurylmethylalanine sodium salt | 25.0 |
| Coconut oil fatty acid potassium salt solution (40%) | 26.0 |
| Coconut oil fatty acid diethanolamide | 3.0 |
| Methylparaben | 0.1 |
| (Component B) | |
| The lactic acid bacteria fermented rice powder obtained in Preparation Example 1 | 10.0 |
| 1,3-Butylene glycol | 2.0 |
| Purified water | the volume to allow a total amount to be 100 parts |

After each of Component A and Component B was homogeneously dissolved by warming it to 80° C., the Component B was added to the, Component A, and the resultant was cooled to room temperature with continuously stirring.

EXAMPLE 19

Antiperspirant (Pressed powder)

| | Part(s) |
|---|---|
| (Component A) | |
| Chlorohydroxyaluminum | 5.0 |
| Zinc oxide | 5.0 |
| The lactic acid bacteria fermented rice powder obtained in Preparation Example 1 | 10.0 |
| Talc | the volume to allow a total amount to be 100 parts |
| (Component B) | |
| Squalane | 3.0 |
| Perfume | q.s. |
| Methylparaben | q.s. |

After Component A was thoroughly mixed, a solution of Component B was uniformly splayed thereover and mixed. The resulting powder was pulverized and then pressed to form.

EXAMPLE 20

Toothpaste

| | Part(s) |
|---|---|
| (Component A) | |
| Dibasic potassium phosphate dihydrate | 60.0 |
| Anhydrous silicic acid | 2.0 |
| Perfume | q.s. |
| (Component B) | |
| Glycerin | 10.0 |
| 1,3-Butylene glycol | 5.0 |
| The lactic acid bacteria fermented rice powder obtained in Preparation Example 1 | 5.0 |
| Sodium lauryl sulfate | 2.0 |
| Carrageenan | 0.3 |
| Methylparaben | q.s. |
| Saccharine sodium | 0.1 |
| Purified water | the volume to allow a total amount to be 100 parts |

Component B was mixed and dissolved by warming it to 80° C., and then cooled to 30° C. To the resultant, Component A was added. The resultant was thoroughly kneaded and then defoamed under reduced pressure.

EXAMPLE 21

Milky lotion

| | Part(s) |
|---|---|
| (Component A) | |
| Liquid paraffin | 5.0 |
| Olive oil | 4.0 |
| Squalane | 5.0 |
| Polyoxyethylene (20) glyceryl monostearate | 1.0 |
| Glyceryl monostearate | 1.0 |
| Butylparaben | 0.1 |

-continued

Milky lotion

| | Part(s) |
|---|---|
| (Component B) | |
| The lactic acid bacteria fermented rice powder obtained in Preparation Example 9 | 3.0 |
| 1,3-Butylene glycol | 10.0 |
| Methylparaben | 0.1 |
| Purified water | the volume to allow a total amount to be 100 parts |
| (Component C) | |
| Perfume | 0.3 |

After each of Component A and Component B was warmed to 80° C. or higher, the Component B was added to the Component A, and the resultant was stirred and homogenized for 2 minutes with PHYSCOTRON (5000 rpm).

After the resultant was cooled to 50° C., Component C was added thereto. The resultant was mixed with stirring, and further cooled to 30° C. or lower to give a homogenous milky lotion.

EXAMPLE 22

Cream

| | Part(s) |
|---|---|
| (Component A) | |
| Liquid paraffin | 5.0 |
| Olive oil | 4.0 |
| Paraffin | 5.0 |
| Sethanol | 2.0 |
| Polyoxyethylene (20) sorbitan monostearate | 2.0 |
| Sorbitan monostearate | 2.0 |
| Butylparaben | 0.1 |
| (Component B) | |
| The lactic acid bacteria fermented rice powder obtained in Preparation Example 1 | 5.0 |
| 1,3-Butylene glycol | 10.0 |
| Methylparaben | 0.1 |
| Purified water | the volume to allow a total amount to be 100 parts |
| (Component C) | |
| Perfume | 0.3 |

After each of Component A and Component B was warmed to 80° C. or higher, the Component B was added to the Component A, and the resultant was stirred and homogenized for 2 minutes with PHYSCOTRON (5000 rpm).

After the resultant was cooled to 50° C., Component C was added thereto. The resultant was mixed with stirring, and further cooled to 30° C. or lower to give a homogenous cream.

EXAMPLE 23

Milky lotion

| | Part(s) |
|---|---|
| (Component A) | |
| Liquid paraffin | 5.0 |
| Olive oil | 4.0 |
| Squalane | 5.0 |
| Polyoxyethylene (20) glyceryl monostearate | 0.7 |
| Glyceryl monostearate | 1.0 |
| Butylparaben | 0.1 |
| (Component B) | |
| The lactic acid bacteria fermented rice powder obtained in Preparation Example 1 | 3.0 |
| Xanthan gum | 0.2 |
| 1,3-Butylene glycol | 10.0 |
| Methylparaben | 0.1 |
| Purified water | the volume to allow a total amount to be 100 parts |
| (Component C) | |
| Perfume | 0.3 |

After each of Component A and Component B was warmed to 80° C. or higher, the Component B was added to the Component A. The resultant was stirred and homogenized for 2 minutes with PHYSCOTRON (5000 rpm).

After the resultant was cooled to 50° C., Component C was added thereto. The resultant was mixed with stirring and further cooled to 30° C. or lower to give a homogenous milky lotion.

EXAMPLE 24

Face lotion

| | Part(s) |
|---|---|
| (Component A) | |
| Olive oil | 1.0 |
| Polyoxyethylene (5.5) cetyl ether | 0.5 |
| Butylparaben | 0.1 |
| (Component B) | |
| The lactic acid bacteria fermented rice powder obtained in Preparation Example 1 | 1.0 |
| Ethanol | 5.0 |
| Glycerin | 5.0 |
| 1,3-Butylene glycol | 5.0 |
| Methylparaben | 0.1 |
| Purified water | the volume to allow a total amount to be 100 parts |
| (Component C) | |
| Perfume | 0.3 |

After each of Component A and Component B was warmed to 80° C. or higher, the Component B was added to the Component A. The resultant was stirred and homogenized for 2 minutes with PHYSCOTRON (5000 rpm).

After the resultant was cooled to 50° C., Component C was added thereto. The resultant was mixed with stirring and further cooled to 30° C. or lower to give a milk-white face lotion.

EXAMPLE 25

| Essence | |
|---|---|
| | Part(s) |
| (Component A) | |
| Olive oil | 1.0 |
| Polyoxyethylene (5.5) cetyl ether | 0.5 |
| Butylparaben | 0.1 |
| (Component B) | |
| The lactic acid bacteria fermented rice powder obtained in Preparation Example 1 | 2.0 |
| Ethanol | 5.0 |
| Hyaluronic acid | 0.3 |
| 1,3-Butylene glycol | 5.0 |
| Methylparaben | 0.1 |
| Purified water | the volume to allow a total amount to be 100 parts |
| (Component C) | |
| Perfume | 0.3 |

After each of Component A and Component B was warmed to 80° C. or higher, the Component B was added to the Component A. The resultant was stirred and homogenized for 2 minutes with PHYSCOTRON (5000 rpm).

After the resultant was cooled to 50° C., Component C was added thereto. The resultant was mixed with stirring and further cooled to 30° C. or lower to give a milk-white essence.

EXAMPLE 26

| Pack (Peer off) | |
|---|---|
| | Part(s) |
| (Component A) | |
| Polyvinyl alcohol | 15.0 |
| Carboxymethyl cellulose | 2.0 |
| The lactic acid bacteria fermented rice powder obtained in Preparation Example 1 | 5.0 |
| 1,3-Butylene glycol | 5.0 |
| Purified water | the volume to allow a total amount to be 100 parts |
| (Component B) | |
| Ethanol | 15.0 |
| Perfume | q.s. |
| Methylparaben | q.s. |

Component A was mixed and dissolved by warming it to 85° C. After the resultant was cooled to 50° C. or lower, the Component B which was separately mixed and dissolved was added thereto. The resultant was cooled to 30° C. or lower with stirring.

EXAMPLE 27

Milky Lotion

Milky lotion was obtained in the same manner as in EXAMPLE 23 except that 3 parts of the lactic acid bacteria fermented rice powder obtained in Preparation Example 2 was used in Component B of EXAMPLE 23 instead of 3 parts of the lactic acid bacteria fermented rice powder obtained in Preparation Example 1.

EXAMPLE 28

Milky Lotion

Milky lotion was obtained in the same manner as in EXAMPLE 23 except that 3 parts of the lactic acid bacteria fermented rice powder obtained in Preparation Example 3 was used in Component B of EXAMPLE 23 instead of 3 parts of the lactic acid bacteria fermented rice powder obtained in Preparation Example 1.

EXAMPLE 29

Milky Lotion

Milky lotion was obtained in the same manner as in EXAMPLE 23 except that 3 parts of the lactic acid bacteria fermented rice powder obtained in Preparation Example 4 was used in Component B of EXAMPLE 23 instead of 3 parts of the lactic acid bacteria fermented rice powder obtained in Preparation Example 1.

EXAMPLE 30

| Milky lotion | |
|---|---|
| | Part(s) |
| (Component A) | |
| Liquid paraffin | 5.0 |
| Olive oil | 4.0 |
| Squalane | 5.0 |
| Polyoxyethylene (20) glyceryl monostearate | 1.0 |
| Glyceryl monostearate | 1.0 |
| Butylparaben | 0.1 |
| (Component B) | |
| The lactic acid bacteria fermented rice dispersion obtained in Preparation Example 5 | 15.0 |
| 1,3-Butylene glycol | 10.0 |
| Methylparaben | 0.1 |
| Purified water | the volume to allow a total amount to be 100 parts |
| (Component C) | |
| Perfume | 0.3 |

After each of Component A and Component B was warmed to 80° C. or higher, the Component B was added to the Component A. The resultant was stirred and homogenized for 2 minutes with PHYSCOTRON (5000 rpm).

After the resultant was cooled to 50° C., the Component C was added thereto. The resultant was mixed with stirring and further cooled to 30° C. or lower to give a homogenous milky lotion.

EXAMPLE 31

| Milky lotion | |
|---|---|
| | Part(s) |
| (Component A) | |
| Liquid paraffin | 5.0 |
| Olive oil | 4.0 |
| Squalane | 5.0 |
| Polyoxyethylene (20) glyceryl monostearate | 1.0 |
| Glyceryl monostearate | 1.0 |
| Butylparaben | 0.1 |
| (Component B) | |
| The lactic acid bacteria fermented rice powder obtained in Preparation Example 1 | 3.0 |
| 1,3-Butylene glycol | 10.0 |
| Kojic acid | 2.0 |
| Methylparaben | 0.1 |
| Purified water | the volume to allow a total amount to be 100 parts |
| (Component C) | |
| Perfume | 0.3 |

After each of Component A and Component B was warmed to 80° C. or higher, the Component B was added to the Component A. The resultant was stirred and homogenized for 2 minutes with PHYSCOTRON (5000 rpm).

After the resultant was cooled to 50° C., Component C was added thereto. The resultant was mixed with stirring and further cooled to 30° C. or lower to give a homogenous milky lotion.

EXAMPLE 32

Milky Lotion

Milky lotion was obtained in the same manner as in EXAMPLE 31 except that 2.0 parts of L-ascorbic acid-2-glucoside were used in Component B of EXAMPLE 31 instead of 2.0 parts of kojic acid.

EXAMPLE 33

Milky Lotion

Milky lotion was obtained in the same manner as in EXAMPLE 31 except that 3.0 parts of L-ascorbic acid-2-phosphoric acid ester magnesium salt were used in Component B of EXAMPLE 31 instead of 2.0 parts of kojic acid.

EXAMPLE 34

Milky Lotion

Milky lotion was obtained in the same manner as in EXAMPLE 31 except that 2.0 parts of arbutin were used in Component B of EXAMPLE 31 instead of 2.0 parts of kojic acid.

EXAMPLE 35

| Milky lotion | |
|---|---|
| | Part(s) |
| (Component A) | |
| Liquid paraffin | 5.0 |
| Olive oil | 4.0 |
| Squalane | 5.0 |
| Polyoxyethylene (20) glyceryl monostearate | 1.0 |
| Glyceryl monostearate | 1.0 |
| Diisopropylamine dichloroacetate | 0.5 |
| Butylparaben | 0.1 |
| (Component B) | |
| The lactic acid bacteria fermented rice powder obtained in Preparation Example 1 | 3.0 |
| 1,3-Butylene glycol | 10.0 |
| Purified water | the volume to allow a total amount to be 100 parts |
| (Component C) | |
| Perfume | 0.3 |

After each of Component A and Component B was warmed to 80° C. or higher, the Component B was added to the Component A. The resultant was stirred and homogenized for 2 minutes with PHYSCOTRON (5000 rpm).

After the resultant was cooled to 50° C., Component C was added thereto. The resultant was mixed with stirring and further cooled to 30° C. or lower to give a homogenous milky lotion.

EXAMPLE 36

| Milky lotion | |
|---|---|
| | Part(s) |
| (Component A) | |
| Liquid paraffin | 5.0 |
| Olive oil | 4.0 |
| Squalane | 5.0 |
| Polyoxyethylene (20) glyceryl monostearate | 1.0 |
| Glyceryl monostearate | 1.0 |
| γ-Amino-β-hydroxylactic acid | 0.5 |
| Butylparaben | 0.1 |
| (Component B) | |
| The lactic acid bacteria fermented rice powder obtained in Preparation Example 1 | 3.0 |
| 1,3-Butylene glycol | 10.0 |
| Purified water | the volume to allow a total amount to be 100 parts |
| (Component C) | |
| Perfume | 0.3 |

After each of Component A and Component B was warmed to 80° C. or higher, the Component B was added to the Component A. The resultant was stirred and homogenized for 2 minutes with PHYSCOTRON (5000 rpm).

After the resultant was cooled to 50° C., Component C was added thereto. The resultant was mixed with stirring and further cooled to 30° C. or lower to give a homogenous milky lotion.

EXAMPLE 37

Milky lotion

| | Part(s) |
|---|---|
| (Component A) | |
| Liquid paraffin | 5.0 |
| Olive oil | 4.0 |
| Squalane | 5.0 |
| Polyoxyethylene (20) glyceryl monostearate | 1.0 |
| Glyceryl monostearate | 1.0 |
| Diisopropylamine dichloroacetate | 0.5 |
| Butylparaben | 0.1 |
| (Component B) | |
| The lactic acid bacteria fermented rice powder obtained in Preparation Example 1 | 3.0 |
| 1,3-Butylene glycol | 10.0 |
| L-Ascorbic acid-2-glucoside | 2.0 |
| Purified water | the volume to allow a total amount to be 100 parts |
| (Component C) | |
| Perfume | 0.3 |

After each of Component A and Component B was warmed to 80° C. or higher, the Component B was added to the Component A. The resultant was stirred and homogenized for 2 minutes with PHYSCOTRON (5000 rpm).

After the resultant was cooled to 50° C., Component C was added thereto. The resultant was mixed with stirring and further cooled to 30° C. or lower to give a homogenous milky lotion.

EXAMPLE 38

Liquid foundation

| | Part(s) |
|---|---|
| (Component A) | |
| Stearic acid | 2.5 |
| Sethanol | 0.5 |
| Polyoxyethylene (20) glyceryl monostearate | 2.0 |
| Glyceryl monostearate | 2.0 |
| Lanolin | 2.0 |
| Squalane | 3.0 |
| Isopropyl myristate | 8.0 |
| Propylparaben | 0.1 |
| (Component B) | |
| The lactic acid bacteria fermented rice powder obtained in Preparation Example 1 | 3.0 |

-continued

Liquid foundation

| | Part(s) |
|---|---|
| Xanthan gum | 0.3 |
| 1,3-Butylene glycol | 5.0 |
| Triethanolamine | 1.0 |
| Methylparaben | 0.1 |
| Purified water | the volume to allow a total amount to be 100 parts |
| (Component C) | |
| Titanium oxide | 8.0 |
| Talc | 4.0 |
| Coloring pigment | q.s. |
| (Component D) | |
| Perfume | 0.3 |

Component C was mixed and pulverized with a grinder. Component B was mixed, and the pulverized Component C was added thereto. The resultant was homogeneously dispersed with a colloid mill. After each of Component A and the homogeneously dispersed Components B and C was warmed to 80° C., the Component A was added to the Components B and C with stirring, and the resultant was homogenized for 2 minutes with PHYSCOTRON (5000 rpm). After the resultant was cooled to 50° C., Component D was added thereto. The resultant was mixed with stirring and further cooled to 30° C. or lower with stirring.

EXAMPLE 39

Cream foundation

| | Part(s) |
|---|---|
| (Component A) | |
| Stearic acid | 5.0 |
| Sethanol | 2.0 |
| Polyoxyethylene (20) glyceryl monostearate | 2.0 |
| Glyceryl monostearate | 3.0 |
| Fluid paraffin | 5.0 |
| Squalane | 3.0 |
| Isopropyl myristate | 8.0 |
| Propylparaben | 0.1 |
| (Component B) | |
| The lactic acid bacteria fermented rice powder obtained in Preparation Example 1 | 3.0 |
| Sorbitol | 3.0 |
| 1,3-Butylene glycol | 5.0 |
| Triethanolamine | 1.5 |
| Methylparaben | 0.1 |
| Purified water | the volume to allow a total amount to be 100 parts |
| (Component C) | |
| Titanium oxide | 8.0 |
| Talc | 2.0 |
| Kaolin | 5.0 |
| Bentonite | 1.0 |
| Coloring pigment | q.s. |
| (Component D) | |
| Perfume | 0.3 |

Component C was mixed and pulverized with a grinder. Component B was mixed, and the pulverized Component C was added thereto. The resultant was homogeneously dispersed with a colloid mill. After each of Component A and the homogeneously dispersed Components B and C was warmed to 80° C., the Component A was added to the Components B and C with stirring, and the resultant was homogenized for 2 minutes with PHYSCOTRON (5000 rpm). After the resultant was cooled to 50° C., Component D was added thereto. The resultant was mixed stirring and further cooled to 30° C. or lower with stirring.

EXAMPLE 40

Powder foundation

| | Part(s) |
|---|---|
| (Component A) | |
| Sericite | 30.0 |
| Titanium oxide | 10.0 |
| The lactic acid bacteria fermented rice powder obtained in Preparation Example 1 | 20.0 |
| Zinc stearate | 1.0 |
| Red iron oxide | 1.0 |
| Yellow iron oxide | 3.0 |
| Black iron oxide | 0.2 |
| Talc | the volume to allow a total amount to be 100 parts |
| (Component B) | |
| Squalane | 7.0 |
| Octyldodecyl myristate | 4.0 |
| Sorbitan monooleate | 0.5 |
| Methylparaben | q.s. |
| Perfume | q.s. |

After Component A was mixed, Component B which was separately warmed and dissolved was added thereto. The resultant was homogeneously mixed, and the resultant was pulverized with a grinder, and then pressed to form.

EXAMPLE 41

Bath agent

| | Part(s) |
|---|---|
| (Component A) | |
| Ethanol | 5.0 |
| Methylparaben | 0.2 |
| Yellow No. 4 | 0.1 |
| Perfume | 1.5 |
| (Component B) | |
| 1,3-Butylene glycol | 5.0 |
| The lactic acid bacteria fermented rice powder obtained in Preparation Example 1 | 10.0 |
| Purified water | the volume to allow a total amount to be 100 parts |
| (Component C) | |
| Dibasic sodium phosphate | q.s. |

Component B was dissolved by warming it to 85° C., and then cooled to room temperature. Thereto was added the solution which was obtained by mixing and dissolving Component A. After adding Component C, the resultant was adjusted to pH 7.0.

EXAMPLE 42

Bubble bath

| | Part(s) |
|---|---|
| (Component A) | |
| Sodium lauryl sulfate | 5.0 |
| Polyoxyethylene lauryl sulfate ether sodium salt | 25.0 |
| Lauric acid ethanolamide | 5.0 |
| Glycerin | 5.0 |
| 1,3-Butylene glycol | 5.0 |
| The lactic acid bacteria fermented rice powder obtained in Preparation Example 1 | 10.0 |
| Pigment | q.s. |
| Purified water | the volume to allow a total amount to be 100 parts |
| (Component B) | |
| Perfume | q.s. |

Component A was dissolved by warming it to 80° C., and then cooled with stirring. Component B was added to the dissolved Component A at 50° C., and the resultant was further cooled to 30° C. or lower.

EXPERIMENTAL EXAMPLE 1

Emulsion Stability (1)

With respect to the lactic acid bacteria fermented rice powder obtained in Preparation Example 1 and commercially available Johsinko (non-glutinous rice powder) to be used as comparative control, emulsion stability was examined by comparing the emulsified products which were prepared by using them as an emulsifier.

(Experimental Method)

Six kinds of the emulsified products which comprises the components (unit: parts) shown in Table 1 were prepared, and variation per time was observed.

TABLE 1

| | Sample No. | | | | | |
|---|---|---|---|---|---|---|
| | 1 | 2 | 3 | 4 | 5 | 6 |
| Component 1 | | | | | | |
| Olive oil | 20.0 | 20.0 | | | | 20.0 |
| Liquid paraffin | | | 20.0 | | | |
| Squalane | | | | 20.0 | | |
| Parcelin oil | | | | | 20.0 | |
| Component 2 | | | | | | |
| The fermented rice powder obtained in Preparation Example 1 | 2.0 | 5.0 | 5.0 | 5.0 | 5.0 | |
| Non-glutinous rice powder (Comparative Example) | | | | | | 5.0 |
| Component 3 | | | | | | |
| Purified water | 67.8 | 64.8 | 64.8 | 64.8 | 64.8 | 64.8 |

TABLE 1-continued

| | Sample No. | | | | | |
|---|---|---|---|---|---|---|
| | 1 | 2 | 3 | 4 | 5 | 6 |
| Component 4 | | | | | | |
| 1,3-Butylene glycol | 10.0 | 10.0 | 10.0 | 10.0 | 10.0 | 10.0 |
| Component 5 | | | | | | |
| Paraben | 0.2 | 0.2 | 0.2 | 0.2 | 0.2 | 0.2 |

Namely, Component 5 was dissolved in Component 4, and both one of the emulsifiers specified in Component 2 and Component 3 were added thereto. The resultant was mixed and warmed to 80° C. To the resultant was added one of the oily components specified in Component 1, and the resultant was homogenized at 5000 rpm for 2 minutes. The resultant was water-cooled to room temperature with stirring. The resulting emulsified product was put into a 50 ml screw bottle, and the emulsification conditions were visually observed immediately after preparing the product and after preserving the product at room temperature or at 40° C. for 3 months, and variation per time was estimated according to the following criteria. ⊚good ○: Very slight separation was observed after more than 1 month Δ: Slight separation was observed after 2 weeks to 1 month.

X: Complete separation was observed.

(Results)

The results are shown in Table 2.

TABLE 2

| | Emulsification conditions | | |
|---|---|---|---|
| Sample No. | Immediately after preparation | Preservation at room temperature | Preservation at 40° C. |
| 1 | ⊚ | ⊚ | ⊚ |
| 2 | ⊚ | ⊚ | ⊚ |
| 3 | ⊚ | ⊚ | ⊚ |
| 4 | ⊚ | ⊚ | ⊚ |
| 5 | ⊚ | ⊚ | ⊚ |
| 6 | ⊚ | X (Note) | X (Note) |

Note:
Complete separation was observed on the 2nd day.

As shown in Table 2, the emulsified products (Sample Nos. 1, 2, 3, 4 and 5) obtained by using the lactic acid bacteria fermented rice powder obtained in Preparation Example 1 were stable for a long period of time irrespective of the oil components mentioned in Table 1. Contrary to that, stable emulsified product could not be obtained in the case of using ordinary pulverized polished rice (non-glutinous rice powder) which is not fermented by lactic acid bacteria (Sample No. 6).

EXPERIMENTAL EXAMPLE 2

Emulsification Stability (2)

The effect of the combined use of the lactic acid bacteria fermented rice and thickener on the emulsification stability was examined.

(Experimental Method)

Four kinds of the emulsified products which comprises the components (unit: parts) shown in Table 3 were prepared, and variation per time was observed.

TABLE 3

| | Sample No. | | | |
|---|---|---|---|---|
| | 1 | 2 | 3 | 4 |
| Component 1 | | | | |
| Olive oil | 20.0 | 20.0 | 20.0 | 20.0 |
| Component 2 | | | | |
| The fermented rice powder obtained in Preparation Example 1 | 1.0 | 1.0 | 1.0 | 1.0 |
| Component 3 | | | | |
| Purified water | 68.8 | 68.7 | 68.3 | 68.3 |
| Component 4 | | | | |
| 1,3-Butylene glycol | 10.0 | 10.0 | 10.0 | 10.0 |
| Component 5 | | | | |
| Paraben | 0.2 | 0.2 | 0.2 | 0.2 |
| Component 6 | | | | |
| Xanthan gum | | 0.1 | 0.5 | |
| Hyaulonic acid | | | | 0.5 |

Namely, Component 5 was dissolved in Component 4, and one of components specified in Component 6 was added thereto and mixed. Separately, each of the mixture of Components 2 and 3 and Component 1 was warmed to 80° C., and then the mixture of the Components 2 and 3 was added to the Component 1. The resultant was homogenized for 2 minutes with PHYSCOTRON (5000 rpm). To the resultant was added the mixture of the Components 4, 5 and 6, and the mixture was further homogenized for one minute with PHYSCOTRON (5000 rpm) and then water-cooled to room temperature with stirring. Each of the resulting emulsified products was put into each 50 ml screw bottle, and the emulsification conditions were visually observed immediately after preparing the product and after preserving the product at room temperature or at 40° C. for 3 months, and variation per time was estimated according to the same criteria as defined in Experimental Example 1.

(Results)

The results are shown in Table 4.

TABLE 4

| | Emulsification conditions | | |
|---|---|---|---|
| Sample No. | Immediately after preparation | Preservation at room temperature | Preservation at 40° C. |
| 1 | ⊚ | ○ | ○ |
| 2 | ⊚ | ⊚ | ⊚ |
| 3 | ⊚ | ⊚ | ⊚ |
| 4 | ⊚ | ⊚ | ⊚ |

It is clear from the results in Table 4 that the combined use of the lactic acid bacteria fermented rice and a thickener further enhances the stability of the emulsified products.

EXPERIMENTAL EXAMPLE 3

Emulsification Stability (3)

The effect of the lactic acid bacteria fermented rice in the present invention on stability of the emulsification system was examined.

(Samples)
(1) The milky lotion obtained in EXAMPLE 21
(2) The milky lotion which was obtained in the same manner as in EXAMPLE 21 except that purified water was used instead of the lactic acid bacteria fermented rice obtained in Preparation Example 9

COMPARATIVE EXAMPLE

Experimental Method

Each sample was put into each 50 ml screw bottle, and the emulsification conditions were visually observed immediately after preparing the milky lotion and after preserving the milky lotion at room temperature or at 40° C. for 3 months, and variation per time was estimated according to the same criteria as defined in Experimental Example 1.

(Results)
The results are shown in Table 5.

TABLE 5

| Sample | Emulsification conditions | | |
|---|---|---|---|
| | Immediately after preparation | Preservation at room temperature | Preservation at 40° C. |
| Milky lotion of EXAMPLE 21 | ⊚ | ⊚ | ⊚ |
| Milky lotion of Comparative Example | ⊚ | Δ | X |

As shown in Table 5, it was observed that even if the lotion was preserved for a long period of time, the milky lotion (EXAMPLE 21) which contains the lactic acid bacteria fermented rice in the present invention did not cause phase separation and it was excellent in the emulsification stability, whereas the milky lotion of Comparative Example was not sufficient in stability and caused the phase separation from the 14th day under preservation conditions at 40° C.

EXPERIMENTAL EXAMPLE 4

Inhibitory Action on Intracellular Tyrosinase Activity (Experimental Method)
Cultured B16 mouse melanoma cells were seeded at $1 \times 10^4$ cells/well in a 96 wells microplate, and preincubated at 37° C. under 5% $CO_2$ for one day in an Eagle's minimum essential medium (MEM) containing 10% of fetal bovine serum (FBS). The culture medium was replaced with Eagle's MEM containing 10% FBS to which an aqueous solution of 10% of the fermented rice powder of Preparation Example 1 (sample solution) was added at a concentration of 5, 10 or 20%, and the cultivation was carried out for 2 days under the same conditions as mentioned above.
5 mM L-dopa or 0.2% MTT was added to the processed microbial cells solution which was obtained by bringing out the culture solution and adding a surfactant (Triton X-100) thereto. The resultant was subjected to tyrosinase reaction at 37° C. L-Dopa value and MTT value were measured at wavelengths of 490 nm and 570-630 nm respectively by using a microplate reader (Model 1450, manufactured by Bio Rad Co., Ltd.).
For comparison, the same procedure was carried out by adding 2 mM kojic acid instead the sample solution or without adding the sample (blank).

(Results)
The Dopa value and MTT value which were obtained in the above-mentioned experiment are shown in FIG. 1 and FIG. 2, respectively. From the results of FIG. 1 and FIG. 2, it was clear that the lactic acid bacteria fermented rice powder in the present invention significantly inhibits intracellular tyrosinase activity without lowering the cell activity.

EXPERIMENTAL EXAMPLE 5

Pigmentary Deposit Inhibition Test
With respect to the lactic acid bacteria fermented rice powder, the in vivo brightening activity was estimated by the pigmentary deposit inhibition test using guinea pigs.

(Experimental Method)
Colored guinea pig (male, 8-week old) was shaved on the center area (60 mm (length)×30 mm (width)) of the back, and the area was divided into two parts (right and left). A solution (sample solution) to one part and purified water as a control to the other, respectively, were applied at 5 ml per a time in the mornings and evenings for 6 days, said solution being prepared by dissolving in purified water the lactic acid bacteria fermented rice powder obtained in Preparation Example 1 at 5.0%. The parts to be applied were subjected to irradiation with UV-B of 500 $mJ/cm^2$ once a day just before application in the mornings. The degree of pigmentary deposit in the irradiated parts was visually observed in the evening on the 6th day and estimated according to the following criteria.
−: Pigmentary deposit was not observed.
±: Very slight pigmentary deposit was observed.
+: Slight pigmentary deposit was observed.
2+: Moderate pigmentary deposit was observed.
3+: Serious pigmentary deposit was observed.

(Results)
The results are shown in Table 6.

TABLE 6

| Guinea pig No. | Sample | Degree of pigmentary deposit |
|---|---|---|
| 1 | Example 1 | ± |
| | Control | 3+ |
| 2 | Example 1 | ± |
| | Control | 3+ |
| 3 | Example 1 | ± |
| | Control | 3+ |
| 4 | Example 1 | ± |
| | Control | 3+ |
| 5 | Example 1 | ± |
| | Control | 3+ |
| 6 | Example 1 | ± |
| | Control | 3+ |

It is clear from the results of Table 6 that the lactic acid bacteria fermented rice powder in the present invention has effects to prevent pigmentary deposit in the skin which is caused by the exposure to ultraviolet rays.

EXPERIMENTAL EXAMPLE 6

Action on Fibroblast Activating (Experimental Method)
Human corium-derived fibroblast NB1RGB(000824) was seeded at $1 \times 10^4$ cells/well in a 96 well microplate which contains a 0.5% FCS-containing minimum essential medium, and precultivated at 37° C. for one day. To the medium was added an aqueous solution (sample solution) containing 10% of the lactic acid bacteria fermented rice powder obtained in Preparation Example 1 so as to be at a concentration of 5, 10 or 20%, and the resultant was further cultivated at 37° C. for 6 days. 0.2% MTT was added to a processed microbial cells solution which was obtained by bringing out medium and then adding a surfactant (Triton X-100) thereto. After the resultant was kept at 37° C., MTT value was measured at a wavelength of 370-630 nm by using a microplate reader (Model 1450, manufactured by Bio Rad Co., Ltd.).

For comparison, the experiment was carried out in the same manner as described above in the case that glucose (100 mM) or no sample (blank) was added instead of the sample solution.

(Results)

The results are shown in FIG. 3.

As shown in FIG. 3, the lactic acid bacteria fermented rice in the present invention accelerates MTT activity on fibroblasts and has an action to activate the fibroblasts.

EXPERIMENTAL EXAMPLE 7

Acute Toxicity

The lactic acid bacteria fermented rice powder obtained in Preparation Example 1 was orally administered to each of 5 male mice and 5 female mice at a dose of 2000 mg/kg. As a result, neither mortality nor abnormality was observed.

EXPERIMENTAL EXAMPLE 8

Irritability to Skin (1)

Each of the following Components was added to hydrophilic petrolatum (Japanese pharmacopoeia) at a concentration of 5%, and the mixture was kneaded to give a sample.

(1) The lactic acid bacteria fermented rice powder obtained in Preparation Example 1 (Sample of the present invention)

(2) Polyoxyethylene (20) sorbitan monooleate (Comparative sample a)

(3) Lipophilic glyceryl monostearate (Comparative sample b)

(4) Glyceryl oleate (Comparative sample c)

(5) Polyoxyethylene (5) lauryl ether (Comparative sample d)

(Experimental Method)

Five adult men (20 to 50 years old) were subjects. Sebum inner the upper arms was wiped off with ethanol, and then the patch obtained by applying 0.2 g of each sample on aluminum foil of Finn Chambers on Scanpor was affixed to the wiped skin area. After 24 hours, the Finn Chambers on Scanpor was removed, and the degree of irritability to the skin was estimated according to the method and criteria which are described below.

(Judge)

1, 24 and 48 hours after removing the patch, the conditions of erythema and edema in the affixed area were visually judged according to the following "criteria of irritability to the skin by Draize test", and the average value of 5 subjects was calculated.

| Score | Conditions of the skin |
|---|---|
| (Erythema) | |
| 0 | no erythema |
| 1 | very slight erythema |
| 2 | distinct eryhema |
| 3 | moderate or severe erythma |
| 4 | slight incrustation on scarlet severe erythma |
| (Edema) | |
| 1 | no edema |
| 2 | very slight edema |
| 3 | distinct edema (clearly distinguishable from the surrounding) |
| 4 | moderate edema (a swelling of 1 mm or more high) |
| 5 | severe edema (spreading over the surrounding) |

(Results)

The results are shown in Table 7.

TABLE 7

| Sample | Scores (erythema + edema (total)) (note) | | |
|---|---|---|---|
| | 1 hour later | 24 hours later | 48 hours later |
| Sample of the present invention | 0 + 0 (0) | 0 + 0 (0) | 0 + 0 (0) |
| Comparative sample a | 1.2 + 0.2 (1.4) | 0.6 + 0 (0.6) | 0 + 0 (0) |
| Comparative sample b | 0.8 + 0 (0.8) | 0.2 + 0 (0.2) | 0 + 0 (0) |
| Comparative sample c | 0.8 + 0.2 (1.0) | 0.6 + 0 (0.6) | 0 + 0 (0) |
| Comparative sample d | 2.2 + 0.8 (3.0) | 1.2 + 0 (1.2) | 0.2 + 0 (0.2) |

(note)
Average of 5 subjects

The surface active agents (a to d) which were used as the comparative sample in the experiment are said to be relatively harmless and are conventionally used for emulsifying cosmetics. However, the results of Table 7 clearly show that the lactic acid bacteria fermented rice powder in the present invention is significantly excellent in safety because it is less irritant to the skin than the above activating agents.

EXPERIMENTAL EXAMPLE 9

Irritability to Skin (2)

Each of the following components was added to hydrophilic petrolatum (Japanese pharmacopoeia) at a concentration of 5%, and the mixture was kneaded to give a sample.

(1) Hydrophilic petrolatum (Japanese pharmacopoeia) (Control)

(2) The lactic acid bacteria fermented rice powder obtained in Preparation Example 1 (Sample of the present invention)

(3) Alubutin (Comparative sample a)

(4) Kojic acid (Comparative sample b)

(Experimental method) and (Judge)

The experiment was carried out in the same manner as in Experimental Example 8 and the judge was carried out according to the criterion described in Experimental Example 8.

(Results)

The results are shown in Table 8.

TABLE 8

| Sample | Scores (erythema + edema (total)) (note) | | |
|---|---|---|---|
| | 1 hour later | 24 hours later | 48 hours later |
| Control | 0 + 0 (0) | 0 + 0 (0) | 0 + 0 (0) |
| Sample of the present invention | 0 + 0 (0) | 0 + 0 (0) | 0 + 0 (0) |
| Comparative sample a | 1.2 + 0 (1.4) | 0.6 + 0 (0.6) | 0 + 0 (0) |
| Comparative sample b | 0.8 + 0 (0.8) | 0.2 + 0 (0.2) | 0 + 0 (0) |

(note)
Average of 5 subjects

The skin brightening agents (a-b) which were used as the comparative sample in the experiment are relatively harmless, and therefore, are conventionally used for skin brightening cosmetics. However, the results of Table 8 clearly show that the lactic acid bacteria fermented rice powder in the present invention is significantly excellent in safety because it is less irritable to the skin than the conventional skin brightening agent.

EXPERIMENTAL EXAMPLE 10

Monitor Test (1)

Feeling when using and safety (irritability etc.) were estimated on the basis of the practical use test by monitors, with respect to the milky lotion of EXAMPLE 2 which was obtained by using the lactic acid bacteria fermented rice powder in the present invention as an emulsifier (single use of the lactic acid bacteria fermented rice powder) and the milky lotion of EXAMPLE 10 (combined use of the lactic acid bacteria fermented rice powder and a thickener).

(Experimental Method)

20 women (20-40 years old) who were selected at random were panelists. Each of the milky lotions of EXAMPLEs 2 and 10 was separately applied, using at different time, to cheeks in face twice a day in the mornings and evenings for 5 days, and the feeling when using, irritability and the like were estimated with respect to each of the following items.

The estimation was carried out on the basis of five ranks (A: good, B: slightly good, C: average, D: slightly bad, E: bad) with respect to the feeling when using and skin conditions, and according to three rank (A: without irritation, B: with discomfort, C: with irritation) as respect to irritability.

(Feeling when Using)
(1) hand feeling
(2) spread when applying
(3) smoothness when applying
(4) permeability (feeling of penetration)
(5) feeling after applying
(Skin Conditions)
(6) skin conditions after applying
(Irritability)
(7) irritation when applying
(8) irritation after applying (Results)

The results are shown in Tables 9 and 10.

TABLE 9

| | Evaluation item | | | | | | | | |
|---|---|---|---|---|---|---|---|---|---|
| | Milky lotion of EXAMPLE 2 | | | | | Milky lotion of EXAMPLE 10 | | | |
| | A | B | C | D | E | A | B | C | D | E |
| Feeling when using (1) | 10 | 4 | 5 | 1 | 0 | 8 | 4 | 6 | 2 | 0 |
| Feeling when using (2) | 9 | 4 | 5 | 2 | 0 | 12 | 5 | 3 | 0 | 0 |
| Feeling when using (3) | 10 | 5 | 3 | 2 | 0 | 12 | 5 | 3 | 0 | 0 |
| Feeling when using (4) | 10 | 6 | 4 | 0 | 0 | 9 | 5 | 4 | 2 | 0 |
| Feeling when using (5) | 10 | 5 | 5 | 0 | 0 | 10 | 7 | 3 | 0 | 0 |
| (6) Conditions of skin | 12 | 3 | 5 | 0 | 0 | 13 | 4 | 3 | 0 | 0 |

TABLE 10

| | Evaluation item | | | | | |
|---|---|---|---|---|---|---|
| | Milky lotion of EXAMPLE 2 | | | Milky lotion of EXAMPLE 10 | | |
| | A | B | C | A | B | C |
| (7) Irritation when applying | 20 | 0 | 0 | 20 | 0 | 0 |
| (8) Irritation after applying | 20 | 0 | 0 | 20 | 0 | 0 |

As shown in Table 9 and Table 10, both of the milky lotions of EXAMPLEs 2 and 10 which were prepared by using the lactic acid bacteria fermented rice as a emulsifier got high estimation points with respect to feeling when using and gave no irritation to the skin.

EXPERIMENTAL EXAMPLE 11

Monitor Test (2)

The effect on hair was estimated by half head test with respect to the cream rinse of EXAMPLE 16 which contains the lactic acid bacteria fermented rice in the present invention and the cream rinse (Comparative Example) which was obtained for comparison by using purified water instead of the lactic acid bacteria fermented rice powder in EXAMPLE 16.

(Experimental Method)

20 women (20 to 40 years old) who were selected at random were panelists. Each of the cream rinses of EXAMPLE 16 and Comparative Example was applied to hair every day. Ten days later, well-combing property, manageability of hair and gloss of hair were estimated according to the following criteria.
(Well-Combing Property)
A: significantly improved
B: improved
C: no change
D: slightly worsen
E: significantly worsen
(Stylability of Hair)
A: significantly improved
B: improved
C: no change
D: slightly worsen
E: significantly worsen
(Silky Texture of Hair)
A: significantly improved
B: improved
C: no change D: slightly worsen
E: significantly worsen (Results)
The results are shown in Table 11.

TABLE 11

|  | Evaluation item | | | | | | | | |
|---|---|---|---|---|---|---|---|---|---|
|  | Rinse of EXAMPLE 16 | | | | | Rinse of Comparative Example | | | |
|  | A | B | C | D | E | A | B | C | D | E |
| Well combing property | 4 | 11 | 4 | 1 | 0 | 0 | 7 | 10 | 2 | 1 |
| Stylability of hair | 5 | 10 | 3 | 2 | 0 | 0 | 7 | 8 | 3 | 2 |
| Siky texture of hair | 4 | 10 | 5 | 1 | 0 | 0 | 6 | 9 | 3 | 2 |

As can be seen from the results of Table 11, the cream rinse which contains the lactic acid bacteria fermented rice in the present invention improves well-combing property and keeps the hair texture in healthy and good conditions due to the moisturizing activity and hair-protecting activity of the lactic acid bacteria fermented rice to be added as a component.

Additionally, the cream rinse of the present invention produces creamy foam which is soft, and got high estimation points with respect to feeling when using.

EXPERIMENTAL EXAMPLE 12

Monitor Test (3)

With respect to the following samples, the inhibitory effects on pigmentary deposit and irritability to the skin were examined by a monitor test.

(Samples)
(1) Milky lotion of EXAMPLE 2 (The present invention)
(2) Milky lotion which was obtained by using purified water in EXAMPLE 31 instead of the lactic acid bacteria fermented rice powder obtained in Preparation Example 1 (Comparative Example)
(3) Milky lotion which was obtained by using purified water in EXAMPLE 2 instead of the lactic acid bacteria fermented rice powder obtained in Preparation Example 1 (Control)

(Experimental Method)
Twenty women (18 to 50 years old) who were selected at random were subjects. Each of the milky lotions was applied to left upper arm twice a day (in the mornings and evenings) for one month. Pigmentary deposit in applied part and erythema on the skin were visually observed and estimated according to the following criteria.

(Criteria of Estimation)
(Pigmentary Deposit)
A: disappeared
B: apparently diminished
C: slightly diminished
D: hardly changed
E: contrarily increased
(Erythema)
A: no different from Comparative Example
B: hardly different from Comparative Example
C: Erythema is slightly noticeable as compared with Comparative Example
D: Erythema is considerably noticeable as compared with Comparative Example
E: Erythema is clearly noticeable as compared with Comparative Example (Results)
The results are shown in Table 12.

TABLE 12

|  | Sample | | | | | | | | | |
|---|---|---|---|---|---|---|---|---|---|---|
|  | Estimation of pigmentary deposit | | | | | Estimation of erythema | | | | |
|  | A | B | C | D | E | A | B | C | D | E |
| The present invention | 2 | 7 | 9 | 2 | 0 | 20 | 0 | 0 | 0 | 0 |
| Comparative Example | 0 | 6 | 9 | 5 | 0 | 10 | 5 | 4 | 1 | 0 |
| Control | 0 | 0 | 5 | 13 | 2 | — | — | — | — | — |

As shown in Table 12, the milky lotion of the present invention which contains the lactic acid bacteria fermented rice has preventive effect on pigmentary deposit, and is highly safe because of low irritability to the skin.

INDUSTRIAL APPLICABILITY

The lactic acid bacteria fermented rice used in the present invention is characteristic in that it has not only good emulsifying activity, emulsion stabilizing activity but also water-holding and moisturizing activity as well as protecting and sticking activity on the skin and hair, and that it is low in toxicity and less irritable to the skin because of its rice origin. Therefore, according to the present invention, it is possible to provide an emulsifier which is excellent in emulsion stability and biological safety and to provide cosmetics which are excellent in emulsifying stability and biological safety, which are good in feeling when using and feeling after using, and which are effective for improving the skin texture and hair texture.

Additionally, the lactic acid bacteria fermented rice in the present invention has action for preventing melanin formation and action for activating fibroblasts. Therefore, the cosmetics and the skin brightening and caring agent, which are the present invention, are useful for preventing and improving skin pigmentary deposit such as blotches and freckles and also for preventing skin aging and improving rough dry skin.

The invention claimed is:

1. A method for enhancing the appearance of human skin, comprising the steps of:
   (1) fermenting solid rice as a starting material with lactic acid bacteria under anaerobic conditions, to produce a mixture containing a fermented rice,
   (2) collecting the fermented rice as a solid matter from the mixture by filtration to produce an active component comprising the fermented rice;
   (3) formulating the active component together with conventional cosmetic components to form a cosmetic composition;
   (4) applying the cosmetic composition to a skin surface.

2. The method of claim 1, wherein pigmentary deposit on the skin is reduced.

3. The method of claim 1, wherein skin texture is improved.

4. The method of claim 1, wherein rough dry skin is improved.

5. A method for enhancing the appearance of human skin by reducing pigmentary deposit in human skin, comprising the steps of:

(1) fermenting solid rice as a starting material with lactic acid bacteria under anaerobic conditions, to produce a mixture containing a fermented rice;

(2) collecting the fermented rice as a solid matter from the mixture by filtration to produce an active component comprising a fermented rice; the fermented rice being capable of showing inhibitory action on tyrosinase activity;

(3) formulating the active component together with conventional cosmetic components to form a cosmetic composition; and (4) applying the cosmetic composition to a skin surface;

wherein the appearance of human skin is enhanced by reduction of pigmentary deposit in the skin.

6. A method for improving skin texture or rough dry skin, comprising the steps of:

(1) fermenting solid rice as a starting material with lactic acid bacteria under anaerobic conditions, to produce a mixture containing a fermented rice, (2) collecting the fermented rice as a solid matter from the mixture by filtration to produce an active component comprising a fermented rice; the fermented rice being capable of activating fibroblast, (3) formulating the active component together with conventional cosmetic components to form a cosmetic composition, and (4) applying the cosmetic composition to a skin surface wherein skin texture is improved by activating fibroblasts.

7. The method of claim 1, wherein after collecting the solid matter by filtration, the filtered solid is subjected to drying treatment to produce the active component.

8. The method of claim 5, wherein after collecting the solid matter by filtration, the filtered solid is subjected to drying treatment to produce the active component.

9. The method of claim 6, wherein after collecting the solid matter by filtration, the filtered solid is subjected to drying treatment to produce the active component.

10. The method of claim 1, wherein after collecting the solid matter by filtration, the water content of the filtered solid is adjusted to at most 13% to produce the active component.

11. The method of claim 5, wherein after collecting the solid matter by filtration, the water content of the filtered solid is adjusted to at most 13% to produce the active component.

12. The method of claim 6, wherein after collecting the solid matter by filtration, the water content of the filtered solid is adjusted to at most 13% to produce the active component.

* * * * *